United States Patent [19]

Kehe

[11] Patent Number: 5,423,875
[45] Date of Patent: Jun. 13, 1995

[54] UNIVERSAL MOIST ICE WRAP

[76] Inventor: David Kehe, 5521 Greenville Ave. 104, Dallas, Tex. 75206

[21] Appl. No.: 233,360

[22] Filed: Apr. 26, 1994

[51] Int. Cl.⁶ ............................................. A61F 7/00
[52] U.S. Cl. .................................... 607/112; 607/114
[58] Field of Search ..................... 607/96, 108–112, 607/114

[56] References Cited

U.S. PATENT DOCUMENTS

| | | | |
|---|---|---|---|
| 1,567,931 | 12/1925 | Epler | 607/109 X |
| 3,491,761 | 1/1970 | Baker | 607/112 X |
| 4,081,150 | 3/1978 | Tyson | |
| 4,645,498 | 2/1987 | Kosak | |
| 5,000,176 | 3/1991 | Daniel | |
| 5,086,629 | 2/1992 | Dibrell | |
| 5,197,292 | 3/1993 | McPherson | 607/109 X |

*Primary Examiner*—Angela D. Sykes
*Attorney, Agent, or Firm*—Daniel V. Thompson

[57] ABSTRACT

The universal moist ice wrap is made of two parts, a sleeve designed to allow the crushing and containment of real ice, and an elastic strap called a compression strap which can be used to fasten the sleeve in place and increase cold transmission at the desire of the user. The sleeve is made of two faces, one of water-permeable material and the other of a water-impermeable material, sealed with a watertight edge and one edge opened, which can be closed at will using the Velcro ® edging fastened to the opposing materials. Straps and sleeves may be joined in a series of different combinations to allow the sleeve to be used by humans and animals for cryotherapy at the lowest possible safe temperature which can be applied against the skin.

5 Claims, 4 Drawing Sheets

UNIVERSAL MOIST ICE WRAP

FIELD OF INVENTION

The invention relates to therapeutic devices, and more particularly to a device made of two independent parts which can be used together to deliver cryotherapy to animals and to humans at the lowest possible safe temperature.

DESCRIPTION OF THE INVENTION

It has long been recognized that the application of cryotherapy (cold therapy) can help heal injuries and bring the user relief from discomfort. Generally relief occurs when the intramuscular temperature can be reduced significantly. Because blood circulation makes this interior temperature reduction difficult, a great deal of cold must be applied at the skin level. This creates a risk of frostbite to the skin. When the temperature at the skin level is 32 degrees or less, this risk is very real, and yet temperatures near this level are necessary to cause significant intramuscular temperature reduction. While numerous patents have been issued in the area of cold therapy and ice packs in particular, there has been no effort to address the temperature problem. The invention in its preferred embodiment attempts to fill this very real need for maximum cold with complete safety, unaddressed in the prior art.

SUMMARY OF THE INVENTION

The invention includes a flexible sleeve for ice and a compression strap to allow that sleeve to be applied to any body part with compression. Several sleeves and/or straps may be fastened together to cover different sized areas. The use of real ice, the percolation of melt water from that ice through the sleeve and against the skin, and the compression of the sleeve against the skin by the compression strap to maximize water loss, delivers the lowest possible safe temperature for cold therapy.

A preferred embodiment of the sleeve is made of two rectangular pieces of material, approximately 7 inches wide and 25 inches long, with one of the pieces about an inch longer than the other. The shorter of these pieces is water-permeable, and the longer is water-impermeable. They are placed facing one another, and securely fastened along three edges with a water tight seal. The fourth edge, which forms the mouth of the sleeve, is open. A piece of hook Velcro ® approximately 5 inches by 2 inches is sewed to the back of the impermeable material at the open mouth, and a smaller piece of loop Velcro ® is sewed to the back of the permeable material, adjacent the hook Velcro ®, which allows the user to close the mouth of the sleeve after ice has been inserted. The outward face of the impermeable material has 2¾ inch strips of loop Velcro ® sewn parallel to each other starting at the foot of the sleeve and continuing for about 12 inches. A similar third piece of loop Velcro ® is sewn along the edge of the sleeve adjacent to these strips, which allows two sleeves to be fastened together for about 50 percent of their length. The second element of the invention, the compression strap, in its preferred embodiment is an elastic strap about 24 inches long and 4 inches wide, with hook Velcro ® and loop Velcro ® sewn width-wise across the elastic to allow the strap to be fastened in different positions to the sleeve and/or itself.

This combination allows the application of cold therapy using real ice, on any body part, with a layer of water against the skin to prevent frostbite, and the delivery of cold therapy at the skin at the lowest possible safe temperature for animals or humans.

BRIEF DESCRIPTION OF THE DRAWINGS

A more complete understanding of the invention and its advantages will be apparent from the Detailed Description in conjunction with the Drawings in which.

DETAILED DESCRIPTION OF THE PREFERRED EMBODIMENT

Figure 1:
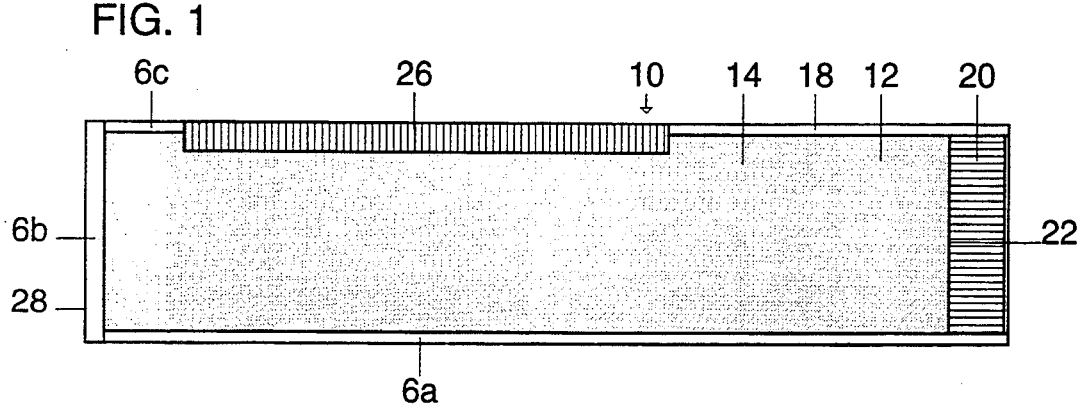
FIG. 1 is a perspective view of the inner side of an ice sleeve showing the water-permeable face.
Figure 2:
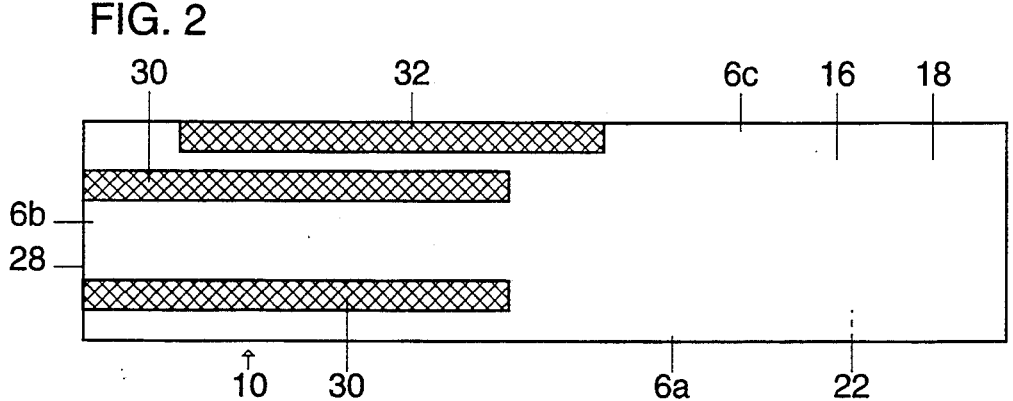
FIG. 2 is a perspective view of the outer side of the ice sleeve of FIG. 1 showing the water-impermeable face.
Figure 3:
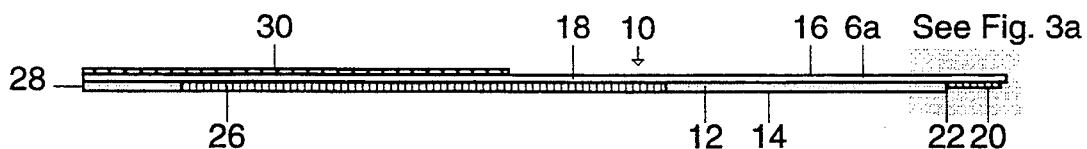
FIG. 3 is a left side view of the ice sleeve showing the position of the Velcro ® strips used to fasten two sleeves together.
Figure 3A:
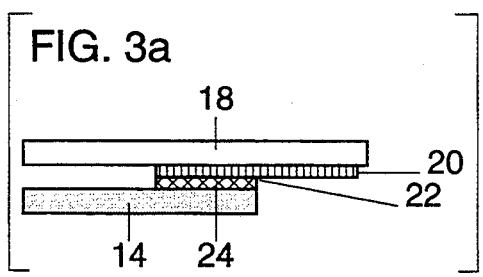
FIG. 3a is a partially broken away, enlarged, side view of a portion of FIG. 3.

Referring initially to FIGS. 1-3a, where like numerals indicate like and corresponding elements, ice sleeve 10 has an inner side 12 which will be applied against the skin. Inner side 12 is composed primarily of a piece of water-permeable material 14. In the preferred embodiment, water-permeable material 14 is nine ounce terry cloth, approximately 7 inches wide and 24 inches long. Outer side 16 is primarily composed of a piece of water-impermeable material 18. Outer side 16 of sleeve 10, which will be applied facing away from the skin, is made of coated nylon in the preferred embodiment. Water-impermeable material 18 is approximately 7 inches wide and 23 inches long, and is placed against water-permeable material 14 and sealed on three edges 6a, 6b, 6c. This sealing system should be water tight and able to withstand the later pressure created when ice is crushed in the sleeve 10 by striking the nylon face of water-impermeable material 18. In the preferred embodiment edges 6a, 6b, 6c are rolled and stitched.

A piece of hook Velcro ® 26, 5 inches by 2 inches, is sewn to the inner face of the water-impermeable material 18, flush with its open end. A smaller 1 inch by 4 inch piece of loop Velcro ® 24 (FIG. 3a) is sewn to the inner face of the water-permeable material 14 so that the inner and outer sides 12, 16 may be fastened shut at the open end 22 when desired.

A piece of hook Velcro ® 26, ¾ inch by 12 inches, is sewn to the inside edge 6c of the water-permeable inner side 12 of the sleeve 10, beginning about 2 inches from the foot 28 of the sleeve 10. Two strips 30 of ¾ inch loop Velcro ®, 12 inches long, are sewn to the outer side 16 beginning at the foot 28 of the sleeve 10 and running parallel in a way which trisects the nylon surface of outer side 16. A third piece 32 of loop Velcro ®, approximately the same size as strip 30, is sewn to the top outer edge 6c of the sleeve 10, beginning 2 inches from the foot 28 of the sleeve 10. This allows two similarly-constructed sleeves 10 to be fastened together for dual use at corresponding strips 26 and 32. A Velcro ® strip 32 of a first sleeve 10 will be connected to the corresponding hook Velcro ® edge 26 on the inner face of an adjacent second sleeve 10.

Figure 4:
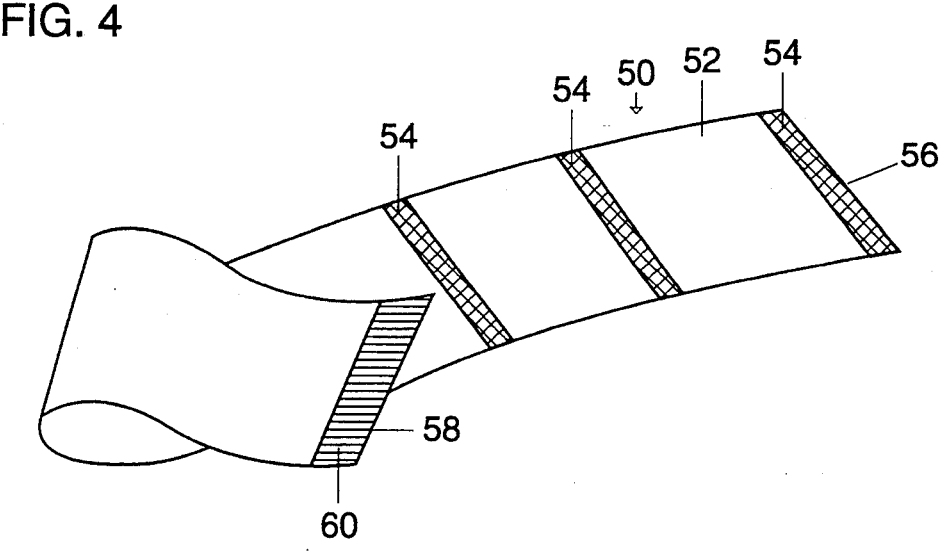
FIG. 4 is a perspective view of the compression strap.

FIG. 4 shows the compression strap 50. In the preferred embodiment this is a strap of elastic 52 measuring 24 inches by 4 inches. Sewn width-wise at variable spacing are ¾ inch by 4 inch strips 54 of loop Velcro ®, beginning at one end 56 of the strap 50. At the opposite end 58 and on the opposite side of the strap 50 is sewn a 1 inch by 4 inch piece of hook Velcro ® 60. These Velcro ® strips 54, 60 allow the strap 50 to be fastened to the sleeve 10 or to itself.

Figure 5:
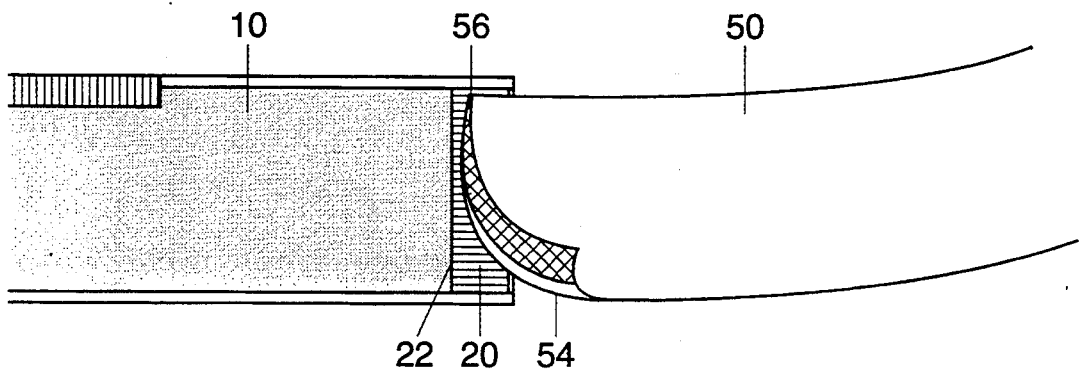
FIG. 5 is a partial perspective view illustrating interface of the ice sleeve and compression strap.

FIG. 5 shows the attachment of the strap 50 to the sleeve 10. One of the loop Velcro ® strips 54 on end 56 of the strap 50 is fastened to the hook Velcro ® strip 20 sewn to the open end 22 of the sleeve 10.

Figure 6:
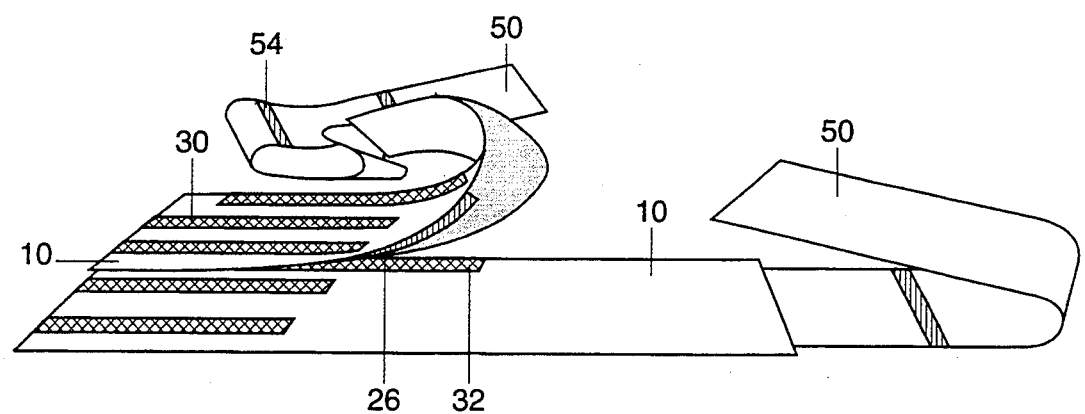
FIG. 6 is a perspective view that shows two ice sleeves fastened to their respective compression straps and interlocked for dual use by means of the Velcro ® edge on each sleeve.

FIG. 6 shows two straps 50 fastened to their respective sleeves 10, and the two sleeves 10 fastened together for dual use. The fastening point of the sleeves 10 is the Velcro ® strip 26 on the inner face of one sleeve 10, and the loop Velcro ® piece 32 on the outer face of the other sleeve 10. This fastening system can be used to create any width of coverage desired by the user through fastening more and more sleeves 10 together. In FIG. 6, the surface area of ice coverage has been doubled.

Figure 7:
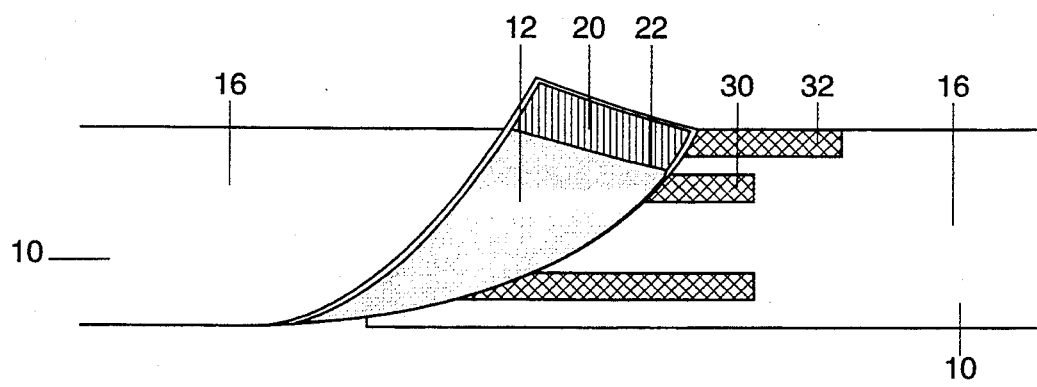
FIG. 7 is a partial perspective view illustrating the interface of two ice sleeves fastened longitudinally.

FIG. 7 shows the connecting of two sleeves 10 joined longitudinally. The Velcro ® strip 20 at the opening 22 of a first sleeve 10 is placed against the loop Velcro ® pieces 30 sewn to the nylon outer side 16 of the second sleeve 10.

Figure 8:
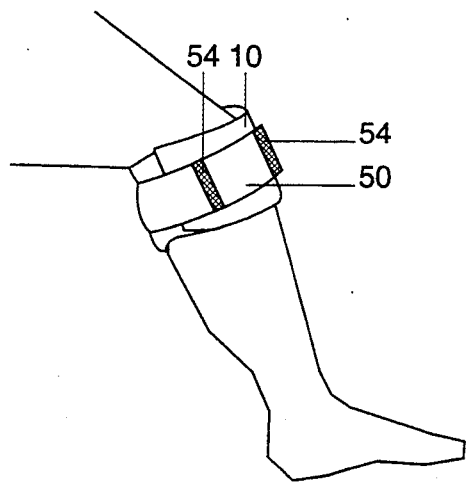
FIG. 8 shows the invention in single use on a knee.

FIG. 8 shows a single sleeve 10 and compression strap 50 in use on a knee. The user inserts a few handfuls of ice in the sleeve 10. He then crushes that ice if desired by striking the nylon outer face 16. The opening 22 of the sleeve 10 is fastened shut using the Velcro ® strips 20, 24 the compression strap 50 is fastened to the Velcro ® strap 20 at the opening of the sleeve 10 using one of the hook Velcro ® strap 54 and the strap 50, and the terry cloth inner face 12 of the sleeve 10 is applied against the area of the knee to be cooled. The ends of the sleeve 10 are wrapped cylindrically around the knee, the compression strap 50 is wrapped around the sleeve 10, and the hook Velcro ® end 60 of the strap 50 is affixed to one of the loop Velcro ® strips 54 on the strap 50 fastening the sleeve 10 securely in place. This strap may be tightened or loosened at will to increase the effective temperature of the sleeve 10 against the skin.

As the ice in the sleeve 10 melts, the melt water is forced by the pressure of the strap 50 and the impermeable quality of the nylon outer layer 18 to percolate through the terry cloth face 14 and come in contact with the skin of the knee, cooling the knee. As the ice continues to melt in the sleeve 10, the compression strap 50 and the nylon layer 18 force new melt water to either wick away into the dry terry cloth or force earlier melt water already in the terry to drip away. The result is a sleeve of ice, separated from the skin by a thin water layer at a temperature of 33 degrees. This low temperature is constantly fed by new 33 degree melt water being forced through the terry. The higher temperature water drips away, and the sleeve continues to percolate fresh melt water against the skin, maintaining this 33 degree temperature until all the ice has liquified.

Figure 9:
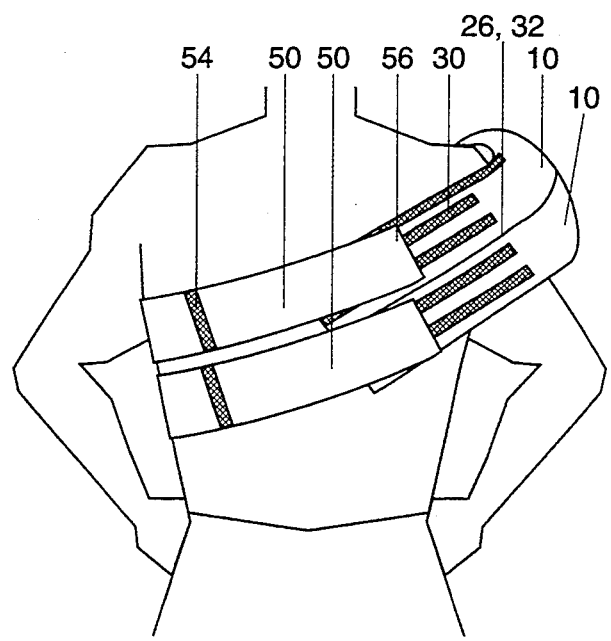
FIG. 9 shows the invention in dual use on a shoulder.

FIG. 9 shows the invention in dual use on the shoulder. The same procedural steps are followed except that two sleeves 10 are fastened together width-wise using the Velcro ® edging 26, 32 as shown in FIG. 6. At the time of application, the terry cloth face 12 is placed against the skin and the straps 50 wrapped around the back. The hook Velcro ® end 56 of the strap 50 is then fastened to the loop Velcro ® strips 30 on the nylon face 18 at the compression level desired by the user.

Figure 10:
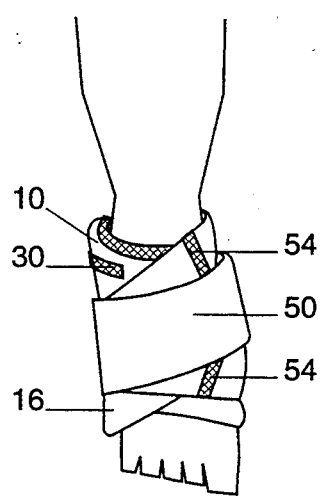
FIG. 10 shows the invention in single use wrapping an ankle.

FIG. 10 shows the invention in single use on an ankle. The middle of the terry cloth face 14 is placed against the Achilles tendon, and the ends laid over the top of the foot. The compression strap 50, already affixed to the sleeve 10, is then wrapped in a figure eight around the bottom of the foot and the back of the ankle. Once again the desired pressure is applied by the user, as the Velcro ® end 56 of the strap is fastened to a selected one of the loop velcro strips 54 on the strap.

It can thus be seen that the primary feature of the invention is a sleeve of opposing materials designed to contain real ice, to utilize the melt water from the ice as safety against frostbite and to maximize water loss for achieving the minimum safe temperature when using the sleeve as a source of cold therapy.

Another important feature is an ice sleeve made of opposing materials and employing an elastic compression strap to force the water from ice melting in the sleeve through the permeable surface of the sleeve and forcing it to drip away from the surface against which the sleeve is fastened, resulting in the lowest possible safe temperature at the skin.

The sleeve made of opposing materials allows ice to be crushed within the sleeve without damage to the materials or their respective qualities of permeability and impermeability.

The strap is made of elastic material which is wide enough to allow the application of uniform compression when wrapped around a surface in conjunction with this sleeve.

The sleeve being made of opposing materials, one being impermeable to water and the other permeable, allows the temperature of the sleeve placed against a surface to be controllable and adjustable through variations in the insulating properties (including thickness) of the permeable material and the pressure with which the sleeve is applied.

Another important feature is a sleeve made of opposing materials which can be fastened in multiple together both widthwise or lengthwise, or both, to create a variable sized permeable surface for the delivery of cold therapy.

Finally, the strap may also be fastened in multiple together lengthwise to allow the use of compression on any size or shape of surface.

I claim:

1. A therapeutic ice sleeve comprising a water-permeable inner side and a water-impermeable outer side;

the inner and outer sides being rectangular and elongate and of substantially the same size along two opposite, long, side edges and one short, closed, end edge, to provide an open cavity along the entire length and width of the ice sleeve;

the outer side being longer than the inner side at an open end opposite the closed end edge and provided with a first closure element flush across the inner face of the outer side end;

a second closure element provided on an open end inside edge of the inner side, to engage the first Velcro® closure element and seal the sleeve, the first Velcro® element being wider than the second closure element such that it extends beyond the inner side open edge; and at least one third closure element on the outer side extending lengthwise on the outer side of the sleeve, engageable with the first closure element portion extending beyond the second closure element, such that the sleeve may be wrapped about a portion of a user's body and fastened by engagement of the first and third closure elements.

2. The ice sleeve of claim 1 with an elastic compression strap for applying compression to a user treatment location;

the compression strap having a fourth closure element engageable with the first closure element portion extending beyond the second closure element, the strap being rectangular and elongate for overwrapping application of compression to the ice sleeve.

3. The ice sleeve of claim 2 with cooperating closure elements on the strap to permit fastening the straps to itself to maintain an overwrapped application.

4. The ice sleeve of claim 2 with a plurality of compression straps attached end to end to enhance the application of compression.

5. A plurality of ice sleeves of claim 1, fastened together to cover a large user treatment location;

the sleeves fastened together by way of cooperating closure elements along portions of the sleeve side edges.

* * * * *